United States Patent [19]
Rich et al.

[11] Patent Number: 6,126,610
[45] Date of Patent: Oct. 3, 2000

[54] PNEUMATIC CONNECTOR WITH ENCODING

[75] Inventors: David R. Rich, Glastonbury; John R. Nobile, Fairfield, both of Conn.

[73] Assignee: Novametrix Medical Systems, Inc., Wallingford, Conn.

[21] Appl. No.: 08/963,336

[22] Filed: Nov. 3, 1997

[51] Int. Cl.[7] ........................................................ A61B 5/00
[52] U.S. Cl. .......................... 600/529; 600/532; 600/538; 128/204.23
[58] Field of Search ..................................... 600/529–538, 600/300–301, 322–323; 439/191–193, 620, 352, 955; 285/124.1, 29, 119; 73/863.53; 128/897–898, 920–925, 204.12–204.23; 138/46

[56] References Cited

U.S. PATENT DOCUMENTS

| | | |
|---|---|---|
| 4,076,279 | 2/1978 | Klotz et al. . |
| 4,989,456 | 2/1991 | Stupecky . |
| 5,197,895 | 3/1993 | Stupecky . |
| 5,405,269 | 4/1995 | Stupecky ................................ 439/195 |
| 5,660,567 | 8/1997 | Nierlich et al. . |
| 5,925,831 | 7/1999 | Storsved . |

*Primary Examiner*—Cary O'Connor
*Assistant Examiner*—Michael Astorino
*Attorney, Agent, or Firm*—Trask Britt

[57] ABSTRACT

A connector for connecting segments of one or more pneumatic tubes including a first member, a second member and a sealing element. The first member and second member are configured to interconnect with each other with the sealing element therebetween. The first member and second member each include at least one cooperating nipple which is insertable into a corresponding port formed through the sealing element. An airtight interference fit is formed between each port and the associated parts of the nipples inserted therein. The connector may also include a mechanism which identifies a type of sensor attached to one of the members to a monitor or other host device attached to the other member. Preferably, the connector also includes an alignment mechanism to ensure proper polarity of pluralities of tube segments associated with each of the first and second members. The connector may also include a keying structure for ensuring that only compatible devices are coupled thereby.

20 Claims, 11 Drawing Sheets

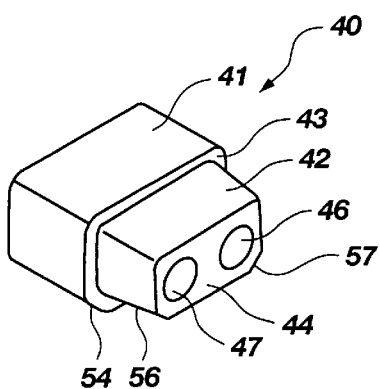
Fig. 4
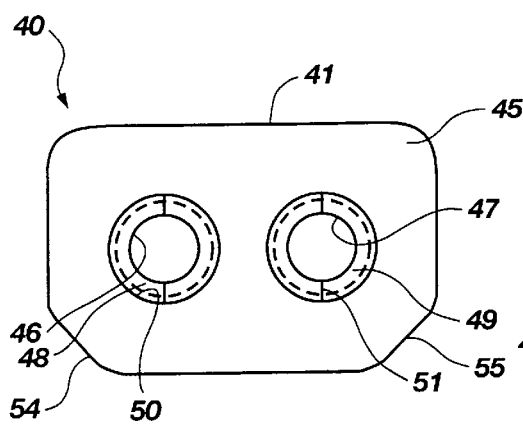
Fig. 4a
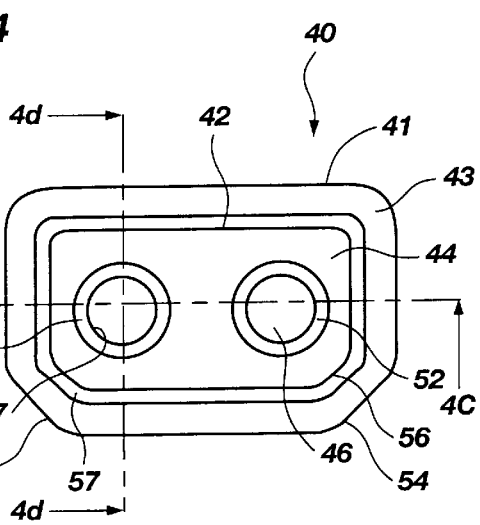
Fig. 4b
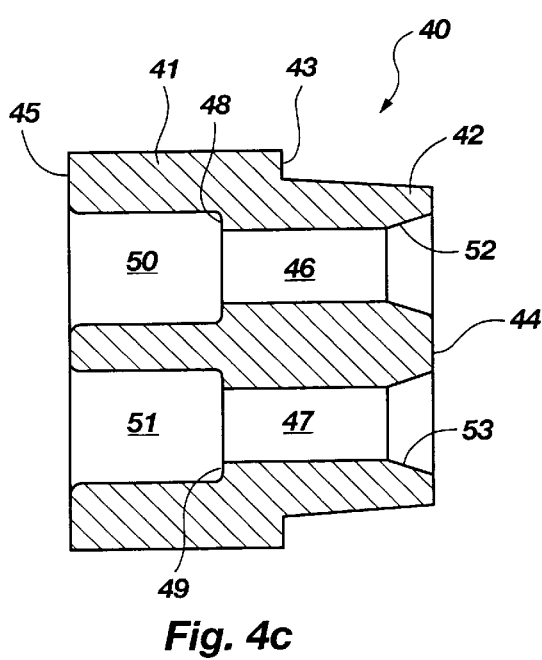
Fig. 4c
Fig. 4d

PNEUMATIC CONNECTOR WITH ENCODING

BACKGROUND OF THE INVENTION

1. Field of the Invention

The present invention relates to pneumatic connectors for use with respiratory sensors, In particular, the present invention relates to pneumatic connectors for securing the ends of mutually laterally adjacent tubes to the ends of other tubes or to another structure. More particularly, the present invention relates to pneumatic connectors which include an indicator mechanism for determining the characteristics of a sensor associated with the tubes being connected to a monitor or other host device. The present invention also relates to pneumatic connectors which include mechanical keying mechanisms thereon.

2. Background of Related Art

Connectors for pneumatic tubing lines are well known. Typically, a pneumatic line connecter includes two coupling members, each attached to an end of a pneumatic tube to be mutually connected with their bores in communication to define a longer fluid line extending through both tubes. Connectors are also employed to connect one or more tubes to a device such as a monitor with transducer, processing, and/or display electronics for sensing, processing and/or displaying one or more parameters of a fluid in the tube or tubes, As the two members are adjoined, they connect the two tubes of a line with a airtight seal. Many such connector devices include hollow nipples, which are insertable into the tube ends, for attaching the tubing thereto. Many devices also employ an interference fit between rigid, mating elements of the two coupling members to provide a tight seal between the two coupling members. Some devices also include relatively complex mechanisms for maintaining the connection. U.S. Pat. No. 4,076,279 (the "'279 patent"), issued to Heinz Klotz and Dietmar Padszuck on Feb. 28, 1978, No. 5,197,895 (the "'895 patent"), issued to Josef J. Stupecky on Mar. 30, 1993, and No. 5,405,269 (the "'269 patent"), issued to Josef J. Stupecky on Apr. 11, 1995, disclose exemplary tubing connection devices. The device of the '279 patent is capable of connecting cooperating pluralities of tubes to form a longer plurality of lines. The device disclosed in both the '895 and '269 patents connects tubes to form one or more fluid lines and connects wires along one or more electrical lines.

Many tubing connectors are undesirable from the standpoint that they fail to maintain a uniform internal diameter along the entire line extending from tube-to-tube, or at a point of entry of a tube into a monitor or other host device. The insertion of nipples into the tubing alters (expands) the internal diameter of the tube at the connected end thereof. Moreover, the nipples of some connectors have a different internal diameter than the tubing attached thereto. Similarly, the use of an interference fit between elements of the two rigid members of a coupling device may also compress a bore of the coupling device and thus constrict a portion of the internal diameter of a connected line. Variation in a tubing line's internal diameter may be especially problematic in applications where flow and pressure are being measured, since abrupt variations may induce false readings of the flow rate and pressure of the sampled gases or other fluids. Further, the aforementioned types of coupling member-to-tube connection may induce significant variations in the relatively small total internal volume of the tubing line and associated devices.

Some coupling devices, such as that disclosed in the '279 patent, lack a mechanism for ensuring that each line connects only to its correct, corresponding line associated with the mating part of the coupling device. In applications where the characteristics of the transported fluid media differ, and where each line has a different destination, the lack of such a mechanism could have detrimental, if not catastrophic, results. For example, the direction of a respiratory gas content sample into a respiratory flow and/or pressure monitor could provide inaccurate flow and/or pressure data.

Many pneumatic connectors lack a mechanism for determining a type or characteristics of a sensor or sampling device associated with a tube or tubes being connected to another tube or tubes or to a monitor or other host device. This is undesirable when a plurality of devices of different structure or fabricated by different manufacturers, all suitable for use with a single monitor, are connectable thereto at the same sockets As those of skill in the relevant arts are aware, such different sensors may provide different air flow, pressure and other physical characteristic readings for the same patient if their characteristics are not "recognized" by the monitor. Stated another ways in order for a monitor to correctly assimilate a sample, it must make adjustments and/or calibrations specific to the type of sensor that was employed to collect the sample in question.

U.S. Pat. No. 5,660,567 (the "'567 patent"), issued to Steve L. Nierlich et al. on Aug. 26, 1997, discloses a connector for a medical sensor which includes an electronic device for encoding a characteristic of the sensor. The encoding device is a resistor which is matched to the specific sensor. Upon determining the type of sensor attached thereto, a monitoring device makes appropriate adjustments to correctly accommodate the output from the sensor However, the sensor type encoding system of the '567 patent is undesirable for several reasons. First, the addition of a resistor for encoding the device type requires at least one additional component as well as an additional manufacturing step in the assembly of each member of the connector. Second, the use of such a resistor requires the alignment of two additional (electric) lines during coupling Third, the resistor contacts are prone to being bent, broken, or otherwise damaged during coupling of the two connector members.

What is needed is a pneumatic connector assembly which includes a reliable, compact, low-cost; easy-to-use mechanism for accurately identifying the type of sensor attached thereto. There is also a need for a pneumatic connection or assembly which maintains a uniform internal diameter along each tubing-connector-tubing line, and which provides and maintains a good seal at relatively high respiratory sampling pressures. Such A device is also needed specifically to connect a plurality of mutually adjacent pneumatic tubes to another plurality of tubes or to the input of a monitor. A pneumatic connector assembly is also needed which includes a mechanical keying mechanism to ensure that only appropriate devices are connected, and that proper "polarity" (i.e., the correct opposing tubing bores are mated) is effected by the connection.

SUMMARY OF THE INVENTION

The pneumatic connector of the present invention addresses each of the foregoing needs with a simple, compact, robust coupling structure, A preferred embodiment of the connection or coupling device of the present invention includes a female attachment member, a sealing element placeable within the female attachment member and a male attachment member which operatively interconnects with the female attachment member, the sealing element being disposed therebetween. Each of the female attachment member and male attachment member have one or more sets of tubes attached thereto in sang relationship therewith. Preferably, the tubes are each secured within a corresponding nipple of an attachment member. As the female and male attachment members are interconnected, corresponding tubes are aligned, and an airtight interconnection is formed therebetween. Thus, in a preferred embodiment of the coupling assembly of the present invention, the male and female attachment members each have the same number of tubes attached thereto.

Preferably, the pneumatic coupling assembly of this invention also includes a mechanism for identifying the type, structure or characteristics of a sensor attached thereto, also referred to generally as a "sensor type" identification mechanism. A preferred sensor type identification mechanism includes an optical sensor attached to one of the male and female attachment members, and a structure on the other of the female and male attachment members which characterizes the type of sensor attached thereto, referred to as a sensor type encoding system. In the preferred embodiment, a system of notches is used to denote the association of a specific type of sensor with that connector member.

A preferred use of the pneumatic connection device of the present invention includes the attachment of one set of lines from a respiratory flow, pressure and carbon dioxide ($CO_2$) sensor to a second set of lines, each of which is operatively interconnected with a respiratory profile monitor.

As noted above, the preferred sensor type identification mechanism for use in the pneumatic coupling device of the present invention includes a series of notches on one connector member. The sealing element, which reflects light differently than the one connector member in which the notches are formed, is exposed through notches of the one connector member upon assembly therewith. When the sealing member and the one connector member are assembled and the two connector members interconnected, the notches of the one connector member and the portions of the sealing member exposed therethrough are exposed through a slot, which is also referred to herein as a sensor type identification window, of the other connector member. Thus, when the connector members and sealing member are assembled and interconnected, the number and arrangement of notches in the one connector member may be detected by an optical sensor placed in close physical proximity with and directed toward the sensor type identification window. Thus, in order to indicate to a monitor a type of sensor attached thereto, the notches and optical sensor need only be close to each other; physical interconnection or contacting of these elements is not necessary. Preferably, the notches are molded into one attachment member of the connector during the manufacture thereof. Therefore, attachment of the optical sensor to the other attachment member requires a single additional assembly step in the manufacture of only one of the connector members.

The sealing element of the pneumatic connector includes holes formed therethrough for receiving nipples projecting from both the male and female attachment members. Upon insertion into a hole of the sealing element, the nipples of each of the members form an interference fit with the bore walls defining the respective portions of the hole into which they are inserted. Preferably, the sealing element is manufactured from a somewhat deformable material with substantially zero compression set, Consequently, the use of an interference fit in the assembly of the present invention does not deform the nipples, constrict the internal bores, or otherwise alter the internal diameter of any of the lines connected thereby. Moreover, the use of such a seating element imparts the connector with the ability to provide an airtight seal and maintain same at relatively high respiratory pressures.

The male and female attachment members also include a structure for ensuring a proper interconnection orientation relative to one, another. In the preferred embodiment, the male and female attachment members each include two corresponding chamfered corners to ensure proper rotational alignment of the connection. The two attachment members may also include interfitting mechanical keying mechanisms, which may also ensure proper polarity of the two members as well as prevent connection of incompatible devices.

Preferably, the device of the present invention is made from plastic. Injection molding processes are preferred for manufacturing each of the parts. Preferably, the assembly includes five easily assembled parts. Thus, it is a consequent advantage that the device of this invention relative to manufacture. The preferred materials and processes also facilitate the manufacture of a relatively compact pneumatic connector.

Other advantages of the present invention will become apparent to those of ordinary skill in the relevant art through a consideration of the appended drawings and the ensuing description.

BRIEF DESCRIPTION OF THE DRAWINGS

FIG. 2e is a cross-section taken along line 2e—2e of FIG. 2a;

FIG. 4 is a frontal perspective view of a preferred seal member of the pneumatic connector of FIG. 1;

FIG. 4a is a rear plan view of the seal member of FIG. 4;

FIG. 4b is a frontal plan view of the seal member of FIG. 4;

FIG. 4c is a cross-section taken along line 4c—4c of FIG. 4b;

FIG. 4d is a cross-section taken along line 4d—4d of FIG. 4b;

FIG. 5e is a cross-section taken along line 5e—5e of FIG. 5a;

DETAILED DESCRIPTION OF THE PREFERRED EMBODIMENTS

Figure 1:
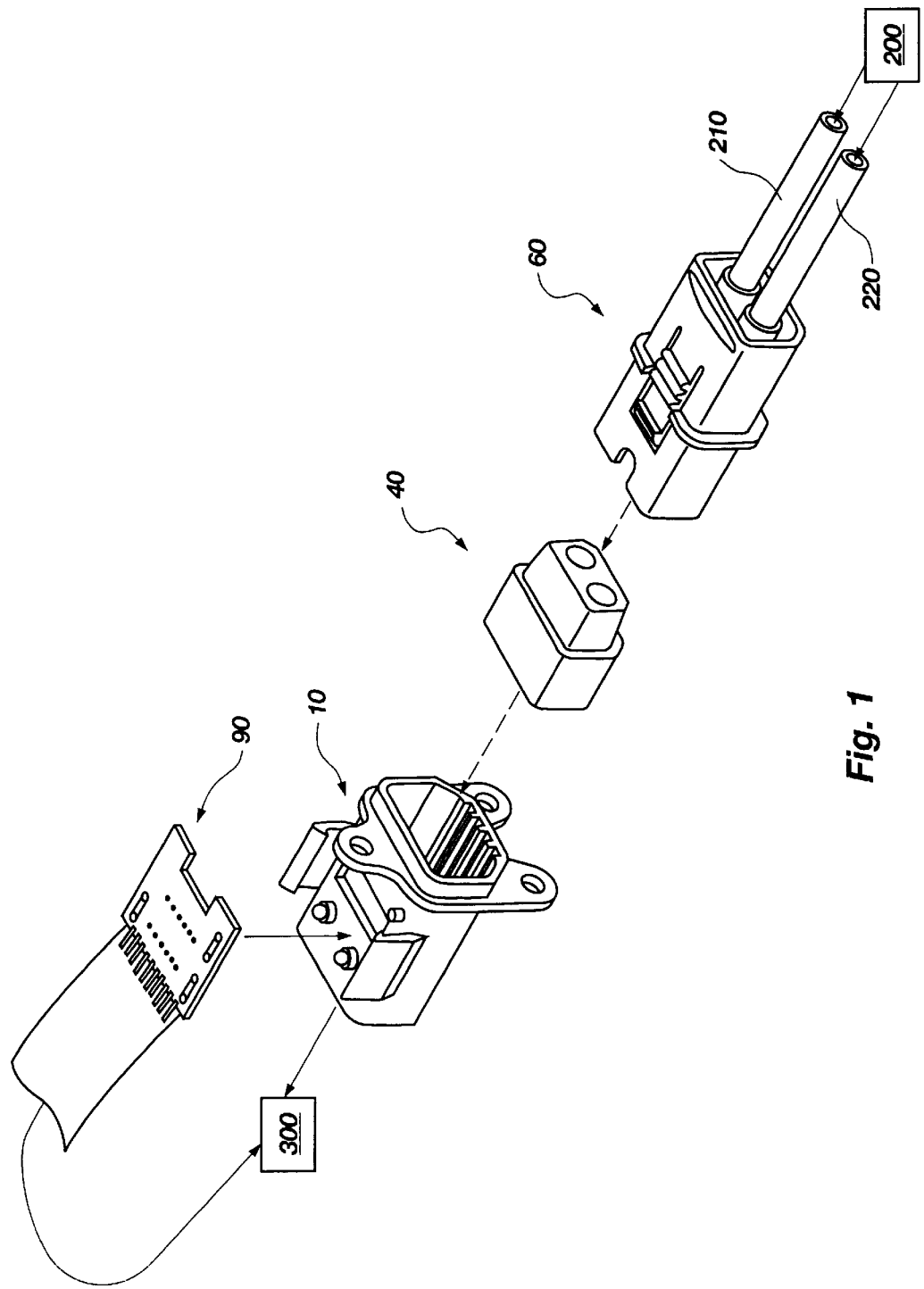
FIG. 1 is a perspective assembly view of a preferred embodiment of the pneumatic connector.
Figure 1A:
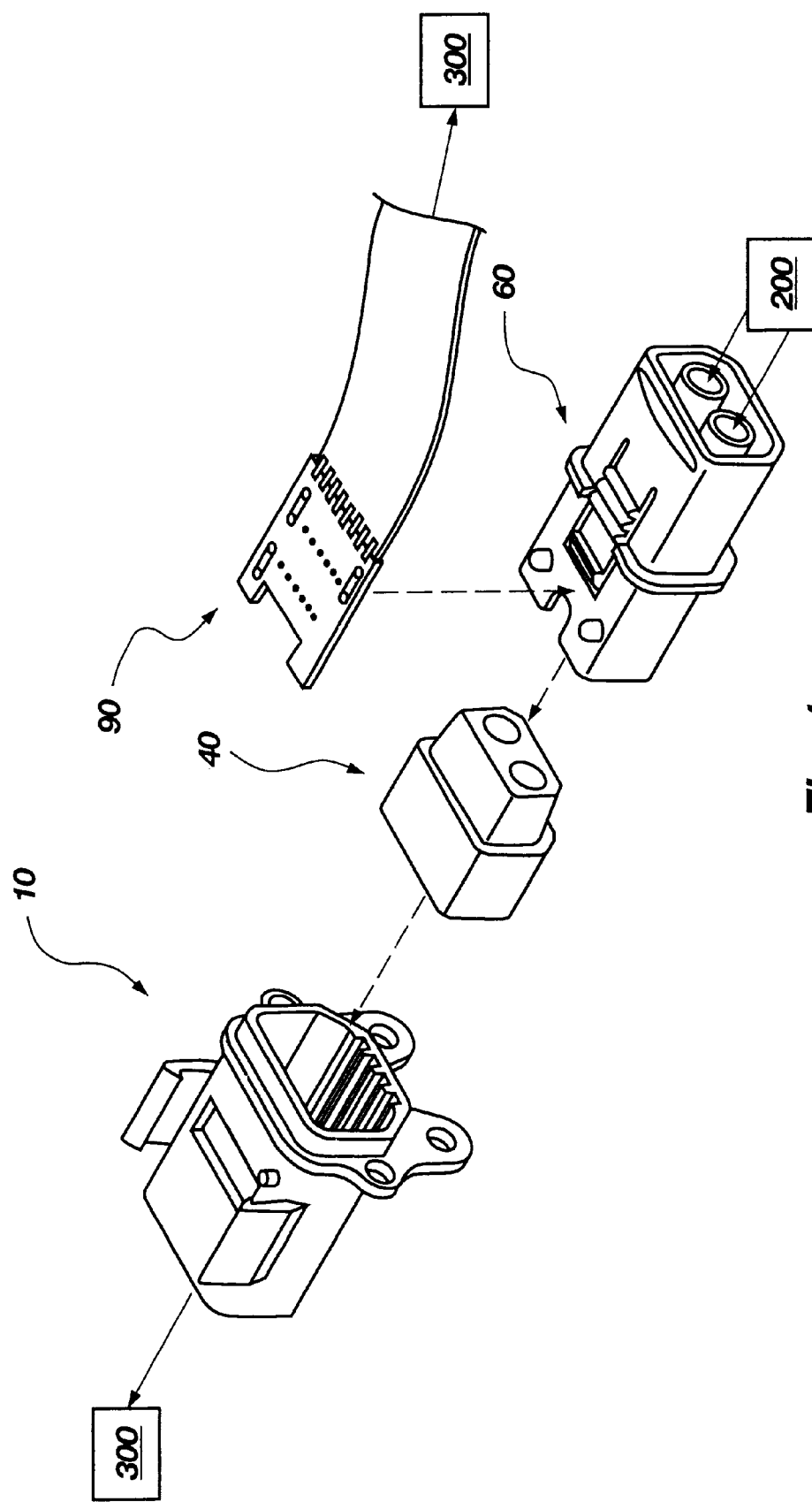
FIG. 1a is a perspective assembly view of another embodiment of the pneumatic connector.

With reference to FIG. 1, a pneumatic connector according to the present invention includes a female attachment member 10, a sealing element 40 placeable within the female attachment member, and a male attachment member 60 which interconnects with the female attachment member. Preferably, the pneumatic connector also includes a optical detector 90, which is attached to female attachment member 10. Female attachment member 10 and optical detector 90 are operably connected to a monitor 300 of a type known in the art, while male attachment member 60 is operably connected to a sensor 200 (e.g., a flow sensor or carbon dioxide pressure sensor) of a type known in the art. Alternatively, as shown in FIG. 1a, optical detector 90 may be secured to male attachment member 60.

Female Attachment Member

Figure 2:
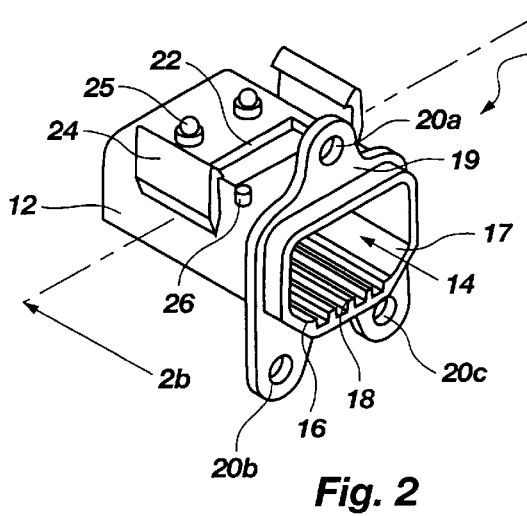
FIG. 2 is a frontal perspective view of a preferred female attachment member of the pneumatic connector of FIG. 1.

Turning now to FIG. 2, a preferred embodiment of female attachment member 10 is shown. FIGS. 2a through 2e also illustrate various views of female attachment member 10. Female attachment member 10 includes a body 12 and a rear wall 13 which form a coupling receptacle 14. Coupling receptacle 14 is adapted to receive a corresponding part of the male attachment member (reference character 60 of FIG. 1), as will be discussed in greater detail below.

Figure 2A:
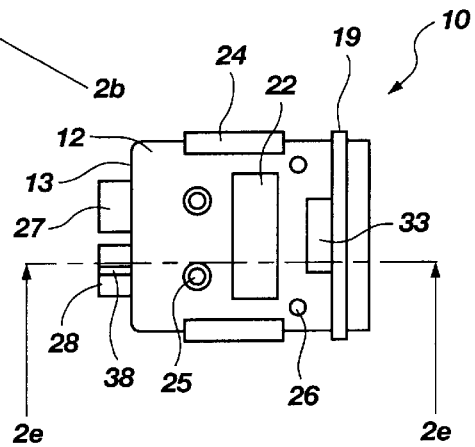
FIG. 2a is a top plan view of the female attachment member of FIG. 2.
Figure 2B:
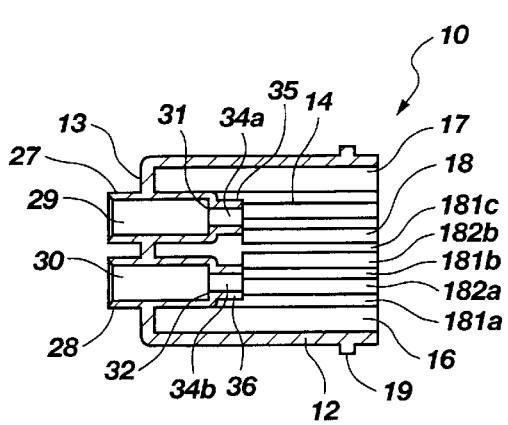
FIG. 2b is a cross-section Hen along line 2b—2b of FIG. 2.

FIG. 2a shows two tube attachment protrusions 27 and 28 extending from rear wall 13. As FIG. 2b illustrates, each of tube attachment protrusions 27 and 28 are hollow members, having a cylindrical tube receptacle 29 and 30, respectively, formed therethrough. A tube (not shown) having an outer diameter of the approximate inner diameter of tube receptacles 29, 30 may be inserted into one of the receptacles up to a tube stop 31 and 32, respectively. Preferably, the tubes are secured within their respective receptacles 29, 30 with a adhesive, solvent, or another method that will create an Might, fluid-tight seal between the tube and the receptacle. The use of adhesives, solvents and other methods of securing the tubes to their respective cylindrical tube receptacles which are known in the art may be used in the present invention.

Nipples 35 and 36, which are respectively continuous and preferably concentric with tube stops 31 32 and cylindrical tube receptacles 29, 30 extend into coupling receptacle 14. Nipples 35 and 36 are also hollow, having flow bores 34a and 34b, respectively, formed therethrough, Plow bores 33a and 33b we continuous with and communicate the passage of fluid to and from the bores of cylindrical tube receptacles 29 and 30, respectively, Referring again to FIG. 2, female attachment member 10 may also include polarity chamfers 16 and 17 formed on the interior of body 12 within coupling receptacle 14. Preferably, polarity chamfers 16 and 17 ensure proper polarity as a corresponding male attachment member (reference character 60 of FIG. 1) is inserted into coupling receptacle 14. Polarity chamfers 16 and 17 are also useful for ensuring that compatible devices are coupled with female attachment member 10, as incompatible devices will have chamfers in incompatible positions, incompatibly shaped chamfers, or a different number of chamfers.

Further, female attachment member 10 may have a mechanical keying mechanism 18 formed in receptacle 14. A preferred mechanical keying mechanism 18 includes a series of teeth 181a, 181b, 181c, etc. defining recesses or notches 182a, 182b, etc. therebetween. Mechanical keying mechanism 18 ensures that only compatible devices are coupled with female attachment member 10. Mechanical keying mechanism 18 may also facilitate the proper alignment of female attachment member 10 with a male attachment member (reference character 60 of FIG. 1) as the two members are longitudinally coupled.

Figure 8:
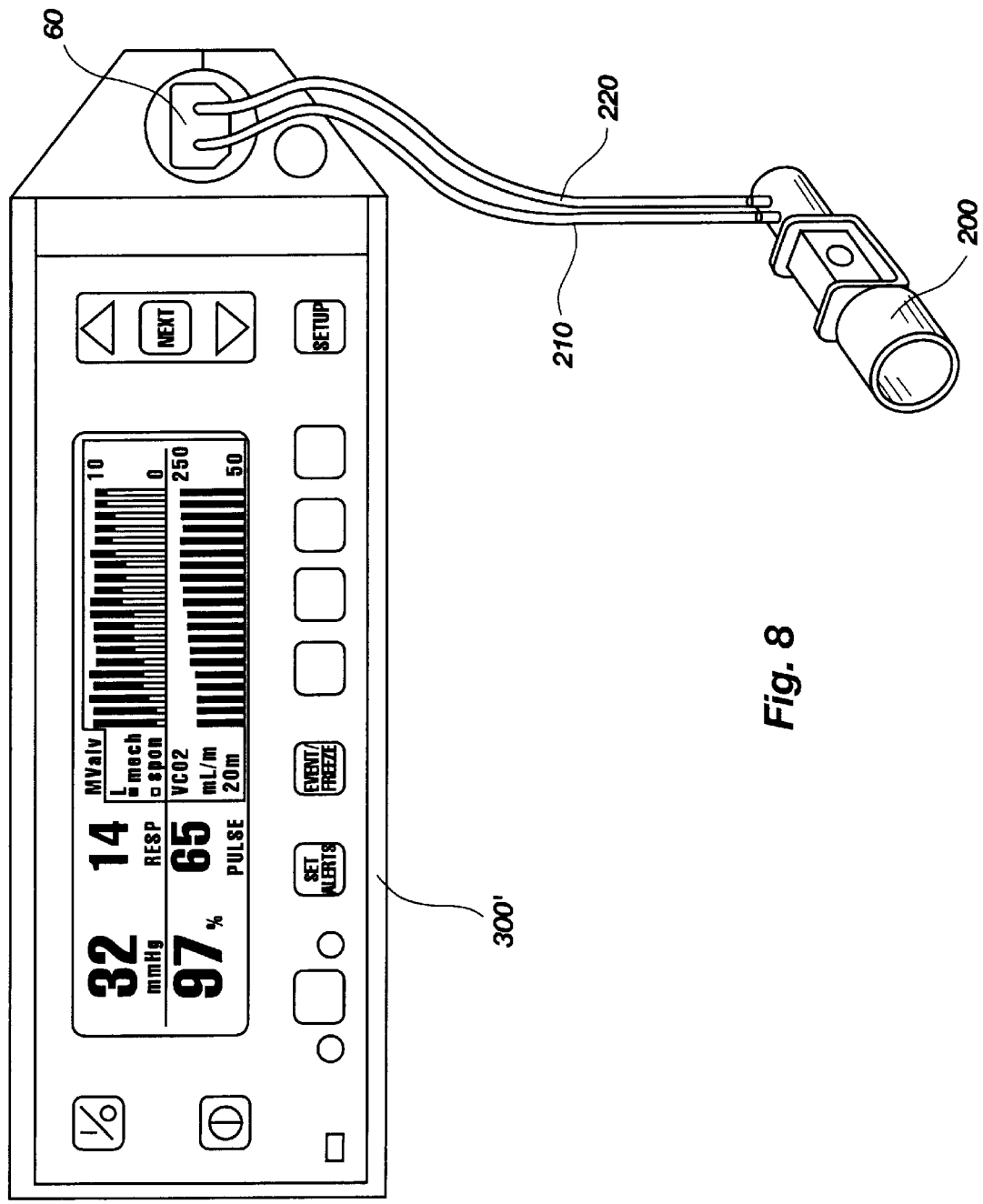
FIG. 8 illustrates the use of the pneumatic connector of FIG. 1 in a respiratory flow, pressure and $CO_2$ monitoring system.

In applications where female attachment member 10 is disposed within or associated with the input of a monitoring device (as illustrated in FIGS. 1 and 8), the female attachment member preferably includes a attachment face 19 extending from body 12. Attachment face 19 includes an attachment mechanism 20, such as the illustrated holes 20a, 20b, and 20c. In the illustrated embodiment, screws, bolts, retaining pins, or the like are inserted through holes 20a, 20b, 20c to secure attachment face 19 and female attachment member, 10 to the monitoring device (not shown).

With continued reference to FIG. 2, a preferred embodiment of female attachment member 10 includes mechanisms for attaching 24 and aligning 25 the sensor (reference character 90 of FIG. 1) on female attachment member 10. Preferably, attachment mechanism 24 includes two resilient clips which extend upward from opposite sides of body 12. Clips 24 spread laterally when optical detector 90 is inserted therebetween, and then snap back together thereover to retain same from vertical movement relative to female attachment member 10. Alignment mechanism 25 preferably includes one or more upwardly extending protrusions from the top of body 12. These protrusions extend through corresponding holes or recesses formed in optical detector 90 to align it and preclude horizontal movement relative to female attachment member 10. Female attachment member 10 may also include one or more supports 26 extending upwardly from body 12. The sensor identification mechanism preferably rests upon supports 26 and upon the enlarged bases of the protrusions of alignment mechanism 25 to restrict downward movement of optical detector 90 relative to the female attachment member 10 and to ensure proper orientation substantially parallel to the longitudinal axis of coupling receptacle 14. Other embodiments of the mechanisms for aligning, attaching and retaining the sensor identification mechanism are also within the scope of the present invention, including without limitation the use of adhesives, screws, and others.

The present embodiment of female attachment member 10 also includes a sensor type identification window 22. Sensor type identification window 22 is an opening formed through the wall of body 12, opening into coupling receptacle 14 to permit the sensor identification mechanism to communicate, detect, or otherwise sense the pressure and type of indicia carried on the male attachment member (reference character 60 of FIG. 1) that denotes the type of sensor attached thereto.

Figure 2C:
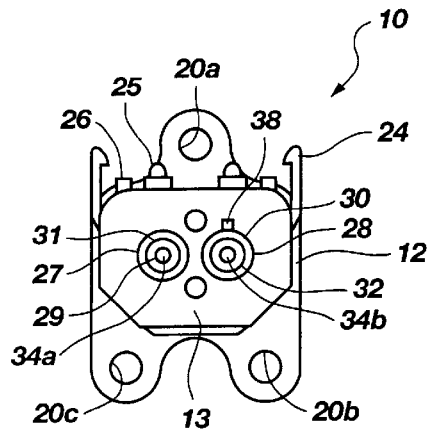
FIG. 2c is a rear plan view of the female attachment member of FIG. 2.
Figure 2D:
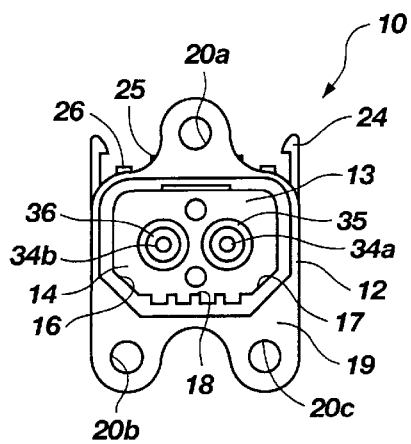
FIG. 2d is a frontal plan view of the female attachment member of FIG. 2.
Figure 2E:
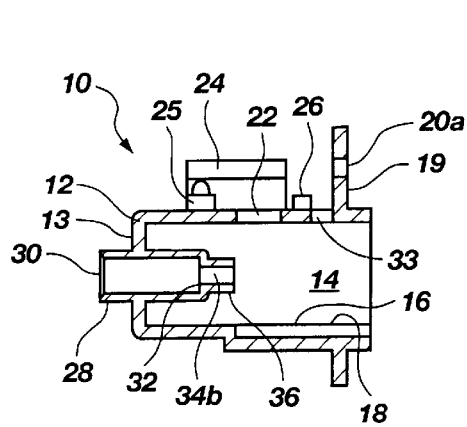

With reference to FIGS. 2a and 2e, female attachment member 10 may include a latching device 33. The latching device 33 illustrated in FIGS. 2a and 2e is a receptacle formed through body 12 for receiving a complimentary latching element of the male attachment member (not shown). Alternatively, a latch element on female attachment member 10 could engage a receptacle formed on the male attachment member 60. Other embodiments of latching devices, including, without limitation, retention pins and receptacles, clips, and others, may also be used in connection with the coupling device of the present invention.

FIGS. 2a and 2c illustrate a reference rib 38 on tube attachment protrusion 28. Reference rib 38 may be included to instruct assemblers and users that a specific tube should be attached to tube attachment protrusion 28 to facilitate proper polarity across the pneumatic connector of the present invention.

A preferred material for manufacturing female attachment member 10 is rigid, durable, impermeable to gas and aqueous liquids, injection moldable, may be formed into small structures, and has good impact resistance. Such materials include, but are not limited to, acrylonitrile butadiene styrene (ABS), polystyrene, styrene acrylonitrile (SAN), and others. An example of ABS which is useful for manufacturing female attachment member 10 is that manufactured by Monsanto as Monsanto 248. Preferably, the material has a light color.

Optical Sensor

Figure 3:
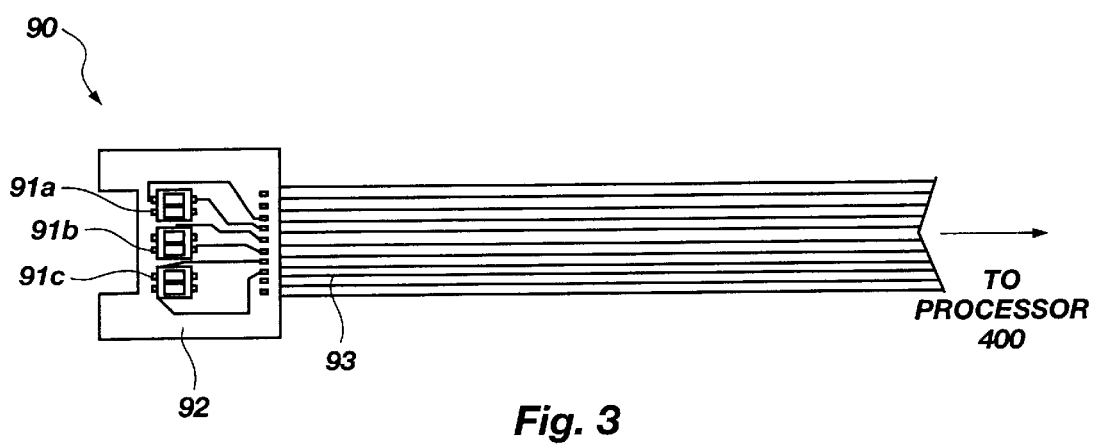
FIG. 3 is a top plan view of an optical sensor for use in the pneumatic connector of FIG. 1.

Referring now to FIG. 3, a preferred embodiment of optical detector 90 is shown. Optical detector 90 includes optical sensors 91a, 91b, 91c which are operatively attached to a circuit board 92. A bus 93 in the form of a flex circuit attaches circuit board 92 to a processor 400 (not shown) employed with the monitor, which identifies the tube and sensor assembly used with the connector of the invention.

Optical sensors 91a, 91b and 91c each sense the presence or absence of reflected light immediately in front of them and generate an electrical signal indicative thereof Typically, light colored objects tend to reflect more light than objects which are of a darker color. Electrical signals indicative of the amount of light reflected at directed to processor 400, which processes the signals to identify a corresponding sensor type from the encoding system (reference character 64 of FIG. 5), or optically readable indicator, which is described in further detail below, carried on male attachment member 60. Known optical sensors are useful i optical detector 90, and the invention herein is not dependent upon the use of any particular brand or type thereof. However, sensors comprising reflective optical encoders are currently preferred.

Circuit board 92 directs the electrical impulses generated by sensors 91a, 91b and 91c to bus 93, preferably comprising a flex circuit formed of metal traces and etched on a dielectric polymer film carrier as known in the art, which conveys those electrical signals to processor 400. Methods for making circuit boards with the desired configuration and number of contacts for the optical sensors are known, Bus 93 includes electrical traces which provide power to and ground optical sensors 91a, 91b and 91c. Electrical buses of the desired size and having the desired number of electrical connections are also known.

Other embodiments of optical detector 90 are also useful, and contemplated to be within the scope of the present invention.

Sealing Element

FIG. 4 depicts a preferred embodiment of sealing element 40, which includes a female nipple insertion end 41 and a male nipple insertion end 42. The preferred embodiment of sealing element 40 also includes two male nipple insertion ports 46 and 47 formed through male nipple insertion end 42 and two female protrusion insertion pots (reference characters 50 and 51 of FIGS. 4a and 4c) formed through female nipple insertion end 41.

Preferably, female nipple insertion end 41 is larger than male nipple insertion end 42. Female nipple insertion end 41 includes a rear side 45. Female nipple insertion end 41 is adapted to insert snugly into the coupling receptacle of the female attachment member (reference character 14 of FIG. 2), with rear side 45 abutting the rear wall (reference character 13 of ° FIG. 2b) of the female attachment member.

The size and shape of male nipple insertion end 42, which preferably tapers to smaller dimensions at front surface 44 of sealing element 40, are adapted to facilitate the insertion of forward extensions of the male attachment member (e.g., the sensor type encoding system 64 and the mechanical keying mechanism 67, shown in FIGS. 5 and 5a through 5k and described in reference thereto) around the outside of the sealing element. Sealing element 40 also includes a shoulder 43 formed around the perimeter thereof, on the front surface of female nipple insertion end 41. Shoulder 43 defines the border between female nipple insertion end 41 and male nipple insertion end 42.

Referring now to FIG. 4c, male nipple insertion ports 46 and 47 are continuous with tube attachment protrusion insertion ports 50 and 51, respectively. Male nipple insertion ports 46 and 47 may each include an outward frustoconical entry taper 52 and 53, respectively, at front surface 44, Thus, the diameters of male nipple insertion ports 46 and 47 increase as they approach front surface 44. Entry tapers 52 and 53 facilitate the insertion of the male nipples (reference characters 78 and 79, respectively, of FIG. 5) into male nipple insertion ports 46 and 47, respectively.

Insertion stops 48 and 49 are formed at the border between female protrusion insertion ports 50 and 51 and male nipple insertion ports 46 and 47, respectively. The diameters of female protrusion insertion ports 50 and 51 are preferably smaller than the outer diameters of the tube attachment protrusions (reference characters 27 and 28, respectively, of FIG. 2a) of the female attachment member. Thus, as the tube attachment protrusions are inserted into female protrusion insertion ports 50 and 51, an airtight interference fit is created between each of the protrusions and sealing element 40.

Similarly, the diameters (inward of entry tapers 52 and 53) of male nipple insertion ports 46 and 47 are slightly smaller than the outer diameters of the corresponding nipples insertable therein, creating an airtight interference fit between each of the nipples of both the male and female attachment members and their respective nipple insertion ports of sealing element 40.

With reference to FIG. 4b, both female nipple insertion end 41 and male nipple insertion end 42 may also include chamfers 54, 55 and 56, 57 respectively, formed thereon. Chamfers 54 and 55 correspond to chamfers (reference characters 16 and 17, respectively, of FIG. 2) of the female attachment member (reference character 10 of FIG. 2) and facilitate insertion of female nipple insertion end 41 into the female attachment member. Chamfers 56 and 57 correspond to chamfers (reference characters 88 and 87, respectively, of FIG. 5) of the male attachment member (reference character 60 of FIG. 5) and facilitate insertion of the male attachment member around male nipple insertion end 42.

A preferred material for manufacturing sealing element 40 is somewhat elastomeric in nature, impermeable to air and aqueous liquid, durable, injection moldable, and has little or no compression set. Such materials include, but are not limited to, urethane, silicone, and other thermoplastic elastomers. A preferred material is an urethane elastomer. Preferably, sealing element 40 is a dark color such as black, for contrast with the white or other light-colored material employed in female attachment member 10 and male attachment member 60 for recognition purposes by optical encoders 91.

Male Attachment Member

Figure 5:
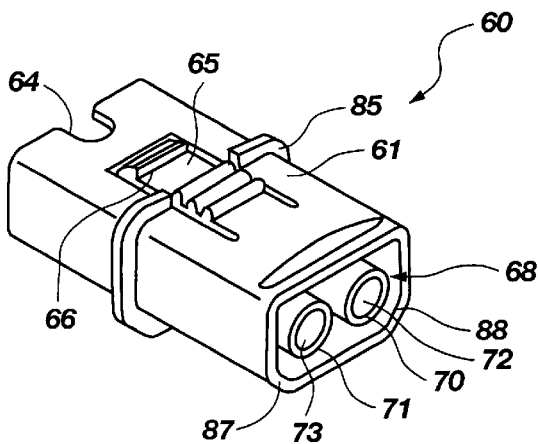
FIG. 5 is a rear perspective view of a preferred male attachment member of the pneumatic connector of FIG. 1.

Referring now to FIG. 5, a preferred embodiment of a male attachment member 60 of the attachment mechanism of the present invention is shown. Male attachment member 60 includes a body 61 having a sealing element receptacle (reference character 62 of FIGS. 5d and 5e) formed in the front end thereof and a tube attachment receptacle 68 formed in the rear end thereof. FIGS. 5c through 5e illustrate a barrier wall 63 which separates sealing element receptacle 62 from tube attachment receptacle 68.

Tube attachment receptacle 68 includes two hollow tube attachment protrusions 70 and 71 therein. Tube receptacles 72 and 73 are formed through the rearward portions of tube attachment protrusions 70 and 71, respectively. With reference to FIG. 5e, the internal end of tube receptacle 72 borders a substantially perpendicularly oriented tube stop 74.

An internal flow port 82, which opens through tube stop 74 to tube receptacle 12, extends through the remainder of tube attachment protrusion 70 and through barrier wall 63, Preferably, internal flow port 82 is coaxial with tube receptacle 72. Internal flow port 82 includes a inward taper 84 as it passes through barrier wall 63. Tube attachment protrusion 71 also includes a tube stop (reference character 75 of FIG. 5c), an internal flow port (not shown), and a taper (not shown) at the forward end of the internal flow port.

With reference to FIG. 5d, sealing element receptacle 62 includes two male nipples 78 and 79, which extend from barrier wall 63. Preferably, each male nipple 78, 79 is a hollow cylindrical protrusion having a nipple flow port 76, 77, respectively, formed therethrough, Referring again to FIG. 5e, forward of its taper, each internal flow port (only port 82 is illustrated in FIG. 5e) opens into and is continuous with a nipple flow port. Thus, nipple flow ports 76 and 77 communicate fluid flow to and from their corresponding internal flow ports. Preferably, each nipple flow port 76, 77 is coaxially aligned with its corresponding internal flow port.

Each nipple flow port 76, 77 preferably has approximately the same diameter as the internal diameter of the tube that is in flow communication therewith. Inward taper 84 and the increased diameter of internal flow port 82 relative to the diameter of nipple flow port 76 and the internal diameter of the tube adjacent thereto accommodate the flow of adhesive, solvent, or the like therein as a tube is inserted into tube receptacle 12, 73. Thus, the pneumatic connector of the present invention maintains a substantially uniform internal diameter along each line passing therethrough.

Referring again to FIG. 1, searing element 40 inserts into coupling receptacle 14 of female attachment member 10. As sealing element 40 is inserted into coupling receptacle 14, female protrusion insertion ports 50 and 51 of the sealing element receive nipples 35 and 36, respectively. Preferably, the outer diameters of nipples 35 and 36 are larger than the diameters of their respective female protrusion insertions ports 50 and 51. Thus, nipples 35 and 36 compress the walls of female protrusion insertions ports 50 and 51 to create an airtight seal therewith. Preferably, the interference fit created between sealing element 40 and nipples 35 and 36 maintains an airtight seal with gas flow pressures therethrough of at least about 2 psi.

Figure 5A:
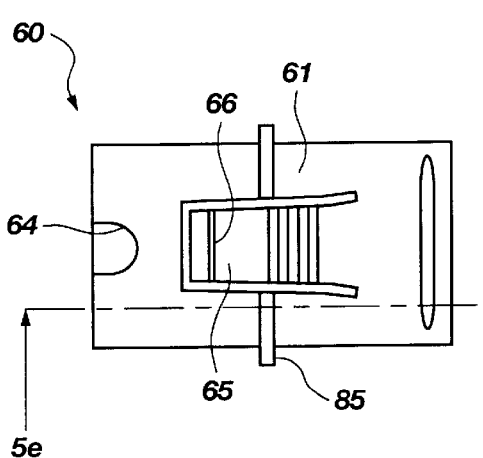
FIG. 5a is a top plan view of the male attachment member of FIG. 5; illustrating a first pattern of a device encoder.

FIGS. 5 and 5a show a preferred embodiment of a sensor type encoding system 64 for use in the pneumatic coupling device of the present invention. Sensor type encoding system 64 includes a series of notches formed through the top of body 61. Sensor type encoding system 64 may include various numbers of notches or arrangements of notches, The width of the notches may also vary with the number of optical sensors 91 employed. Alternative embodiments of sensor type encoding system 64 are also within the scope of the present invention.

FIGS. 5, 5a and 5d illustrate one particular identifying pattern of an encoding system that is useful for denoting the attachment of one type of sensor (not shown) thereto FIGS. 5f through 5k illustrate other patterns 112, 122, 132, 142, 152 and 162, respectively, of the notched sensor type encoding system that are useful for denoting the connection of different devices to otherwise identical male attachment members 110, 120, 130, 140, 150 and 160, respectively. Other sizes, numbers and combinations of the notches may be used to denote the attachment of additional types of sensors to the male attachment member. In the preferred embodiment, a reading of black (i.e., the exterior surface of sealing element 40) by all of the optical sensors (reference characters 91a, 91b and 91c of FIG. 3) denotes that no male attachment member 60, and thus no sensor, is attached to female attachment member 10, Thus, a single, large notch substantially across the width of sensor type encoding system 64 is not used, as it would provide the same reading by sensors 91a through 91b as no connection of a male attachment member 60.

Referring again to FIG. 5, male attachment member 60 may also include polarity chamfers 87 and 88 formed in body 61. Preferably, Polarity chamfers 87 and 88 ensure proper polarity as male attachment member 60 is inserted into the receptacle of a corresponding female attachment member (reference character 10 of FIG. 1). Polarity chamfers 87 and 88 are also useful for ensuring, that male attachment member 60 couples only with a compatible female attachment member 10.

Figure 5B:
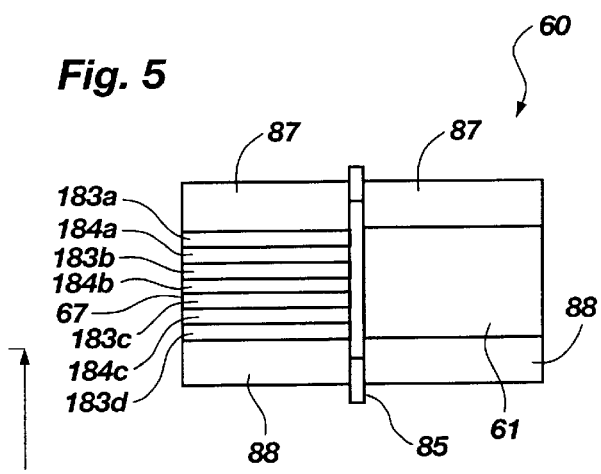
FIG. 5b is a bottom plan view of the male attachment member of FIG. 5.
Figure 5C:
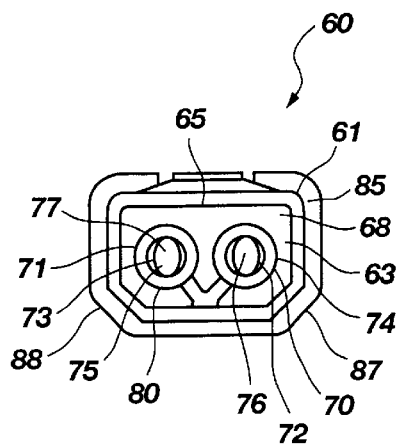
FIG. 5c is a rear plan view of the male attachment member of FIG. 5.
Figure 5D:
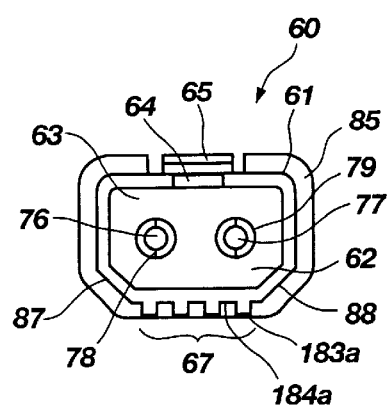
FIG. 5d is a frontal plan view of the male attachment member of FIG. 5.
Figure 5E:
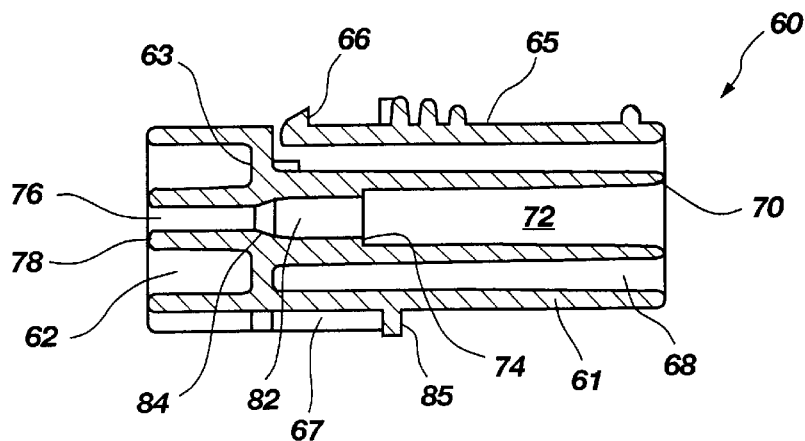
Figure 5F:
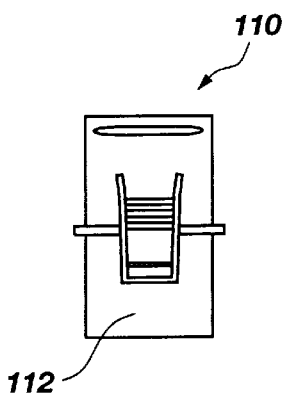
FIGS. 5f through 5k are top plan views of the female attachment member of FIG. 5, illustrating second through seventh patterns, respectively, of a device encoder.
Figure 5G:
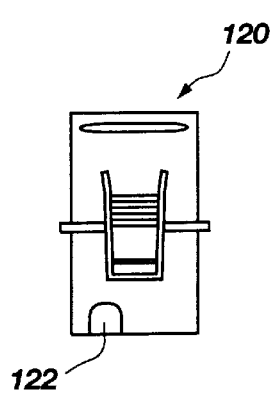
Figure 5H:
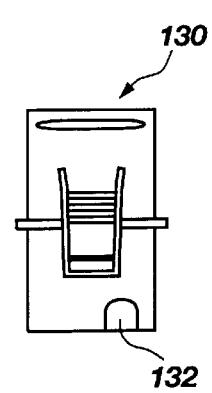
Figure 5I:
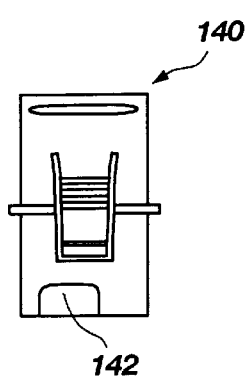
Figure 5J:
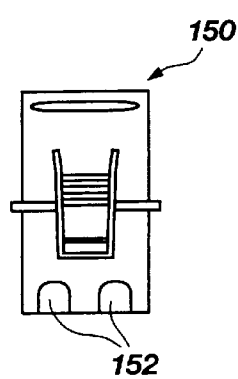
Figure 5K:
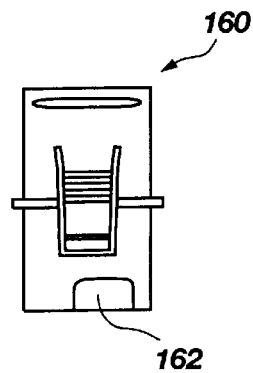
Figure 6:
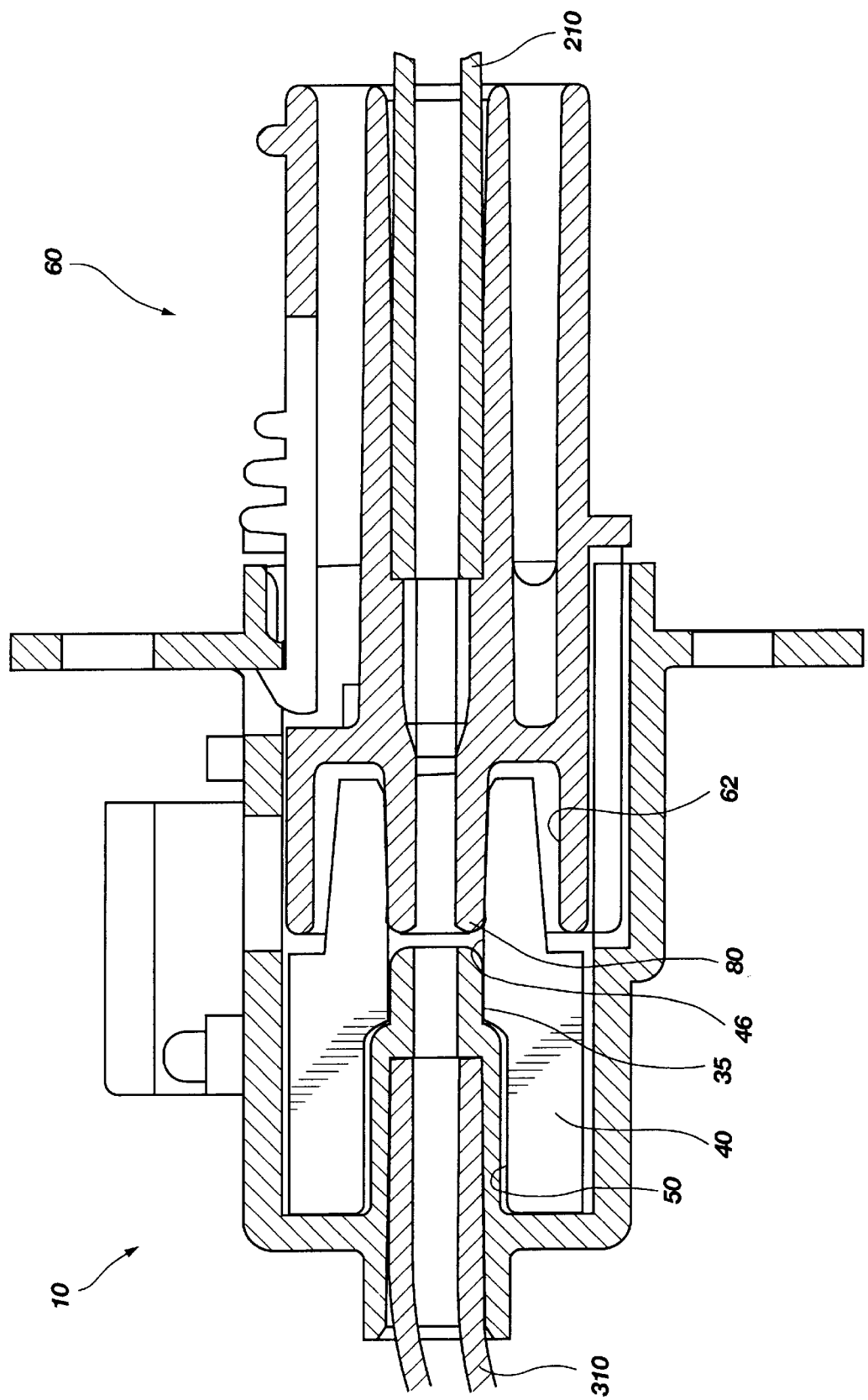
FIG. 6 is a cross-sectional view of the pneumatic connector of FIG. 1, illustrating interconnection of the female and male attachment members thereof.

Similarly, with reference to FIGS. 5b and 5d, male attachment member 60 may carry a mechanical keying mechanism 67 formed on body 61, A preferred mechanical keying mechanism 67 includes a series of teeth 183a, 183b, 183c, etc. defining recesses 184a, 184b, etc. therebetween. Mechanical keying mechanism 67 is configured with an appropriate member, pattern and spacing of teeth 183 to interconnect with the corresponding mechanical keying mechanism 18 of a compatible female attachment member (reference character 10 of FIG. 1). Mechanical keying mechanisms 18 and 67 ensure that only compatible devices are coupled with female attachment member 10, and may also facilitate the proper alignment of the male attachment member 60 with a female attachment member 10 as the two members are coupled.

With reference to FIGS. 5 and 5a, male attachment member 60 may include a latching element 65. The latching element 65 illustrated in FIGS. 5 and 5a is a resilient, downwardly forcible, integrally moldable leaf spring which comprises a latch 66 for engaging a complementary latching device 33 of the female attachment member 10 (see. FIGS. 2a and 2e). As explained above, other embodiments of the latching mechanism may also be used in connection with the coupling device of the present invention.

FIG. 5c illustrates a reference rib 80 on tube attachment protrusion 71. Reference rib 80 may be included to instruct assemblers and users that a specific tube should be attached to tube attachment protrusion 71 and to facilitate proper polarity across the pneumatic connector of the present invention.

Male attachment member 60 may also include a stop 85 extending around body 61 or a portion thereof. Stop 85 prevents male attachment member 60 from inserting too far into the female attachment member (reference character 10 of FIG. 1), and therefore prevents longitudinal compression of the sealing element (reference character 40 of FIG. 1), which could break the seal around the connected nipples.

Preferably male attachment member 60 is manufactured from materials having the sat e characteristics as those that ate used to manufacture the female attachment member 10.

Referring now to FIGS. 2d, 4b, 5d and 6, as an example of the manner of interconnection of female attachment member 10 and male attachment member 60, the male and female attachment members are properly oriented so that Polarity chamfers 87 and 88 and mechanical keying mechanism 67 on male attachment member 60 align with the corresponding Polarity chamfers 16 and 17 and mechanical keying mechanism 18 on female attachment member 10.

Male attachment member 60 is then inserted into coupling receptacle 14 of female attachment member, 10. During insertion, nipples 78 and 79 of male attachment member 60 insert into the respective male nipple insertion ports 46 aid 47 of sealing element 40. A silicone grease or other lubricant may be applied to male nipples 78 and 79 to facilitate insertion of the nipples into male nipple insesrtion ports 46 and 47, respectively, of the sealing element 40. Since the outer diameters of male nipples 78 and 79 are larger than the diameters of male nipple insertion ports 46 and 47, respectively, the nipples radially outwardly compress the walls of the ports to form an airtight seal therewith. The use of a lubricant such as silicone grease may also enhance the seal created between each port and the nipples inserted therein. Preferably, the interference fit created between sealing element 40 and each corresponding set of nipples maintains an airtight seal with gas flow pressures therethrough of at least about 2 psi.

Simultaneously with insertion of male attachment member 60 into coupling receptacle 14 of female attachment member 10, sealing element 40 inserts into sealing element receptacle 62 of male attachment member 60. Upon complete insertion of male nipples 78 and 79 into male nipple insertion ports 46 and 47, respectively, the stop 85 of male attachment member 60 abuts the front surface of female attachment member 10, restricting further insertion of male attachment member 60.

In embodiments of the invented coupling device wherein male attachment member includes latching element 65, latch 66 is forced downward as male attachment member 60 is inserted into coupling receptacle 14 by engagement of the wedge-shaped leading edge of the latch 66 with the outer wall of female attachment member 10. As stop 85 abuts the front surface of female attachment member 10, latch 66 engages an edge of the corresponding latching device (receptacle) 33 on female attachment member 10 as the leading edge of the latch passes under the receptacle and the latch springs back outwardly.

Figure 3A:
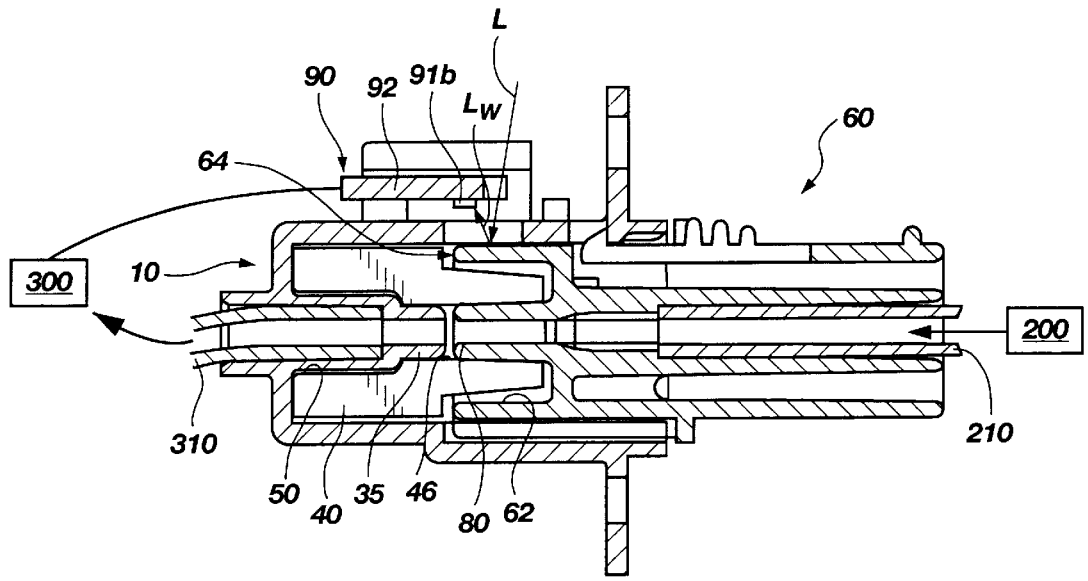
FIGS. 3a and 3b are schematic cross-sectional representations illustrating interconnection of each of the elements of the pneumatic connector and use of the optical sensor and notches in one of the connector members to identify a type of sensor secured to a monitor.
Figure 3B:
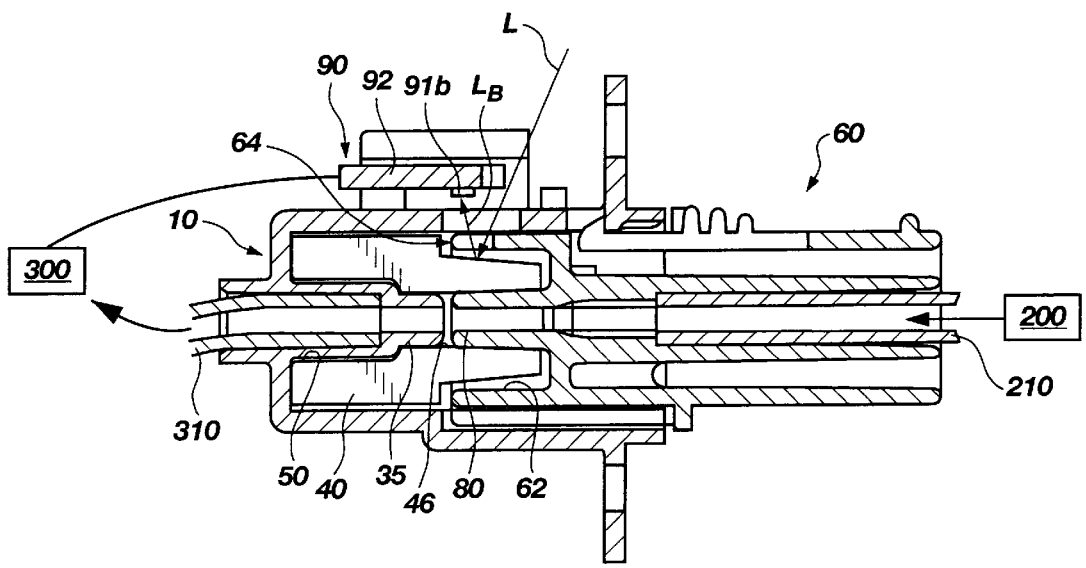

Referring now to FIGS. 3, 3a, and 3b, upon complete insertion of the front portion of male attachment member, 60 into coupling receptacle 14 of female attachment member 10, the particular pattern of the sensor type encoding system 64 of the male attachment member is located directly below and visible through sensor type identification window 22 of female attachment member 10 and sealing element 40 is exposed through any notches of sensor type encoding system 64. In operation of the preferred embodiment of optical detector 90, sensor type encoding system 64 is exposed to light L. Reflective optical sensors 91a, 91b, 91c on the identification mechanism collectively determine the configuration of the corresponding sensor type encoding system 64 on male attachment member 60. In the preferred embodiment of the present invention, male attachment: member 60 is white, while sealing element 40 is black. The: black sealing element 40, which reflects light differently than the sensor type encoding system 64 portion of male attachment member 60, is visible through the notches of sensor type encoding system 64. The white (unnotched) areas of sensor type encoding system 64 adjacent to the notch or notches and the black portions of sealing element 40 that show through the notches are visible through sensor type identification window 22 of female attachment member 10. As each of the three optical sensors 91a, 91b and 91c detects reflected light $L_B$ from the black sealing element 40 (which reflects little or no light) exposed through a notch of sensor type encoding system 64 (FIG. 3b), or reflected light $L_W$ from the white portion of encoding system 64 (FIG. 3a), electrical signals are conveyed to a processor (not shown) of monitor 300, which is adapted to respond to various patterns of notches on sensor type encoding system 64, and therefore confirms the type of sensor attached to male attachment member 60. The processor then calibrates or otherwise adjusts to accommodate the inputs from a particular sensor accordingly. The difference in color of male attachment member 60 from sealing element 40 must be distinguishably different to reflective optical sensors 91a, 91b and 91c (see FIG. 3) of optical detector 90. Thus, using contrasting black and white inputs for optical detector 90 is preferred.

Although the optical detector 90 has been described as including three optical sensors 91, and the corresponding sensor type encoding system 64 has been described as including three notches, fewer than three or more than three optical sensors and a corresponding system of notches may be employed to identify and detect alternative types of sensors.

Use of the Coupling Mechanism

Figure 7:
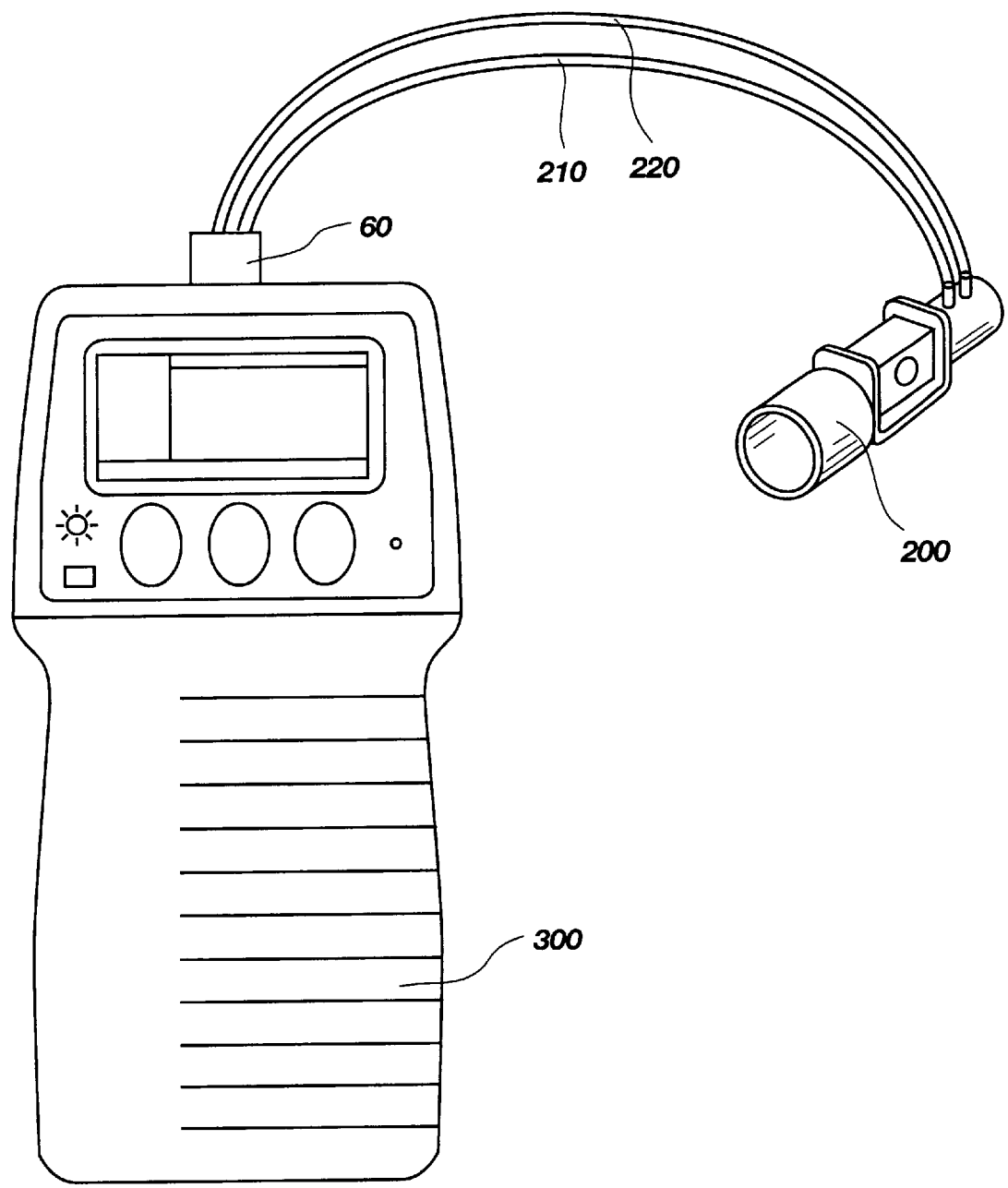
FIG. 7 illustrates the use of the pneumatic connector of FIG. 1 in a respiratory flow and pressure monitoring system.

FIGS. 7 and 8 illustrate the use of the pneumatic connection to couple a respiratory flow sensor 200 to a respiratory profile monitor 300. Tubes 210 and 220 convey respiratory air samples from respiratory flow sensor 200 to male attachment member 60. Male attachment member 60 is attachable to Female attachment member (not shown). The female attachment member has tubes (not shown) attached thereto, which correspond to tubes 210 and 220 and transport respiratory samples into respiratory profile monitor 300. The sensor type identification mechanism (not shown) detects the configuration of the sensor type encoding system on male attachment member 60, as described above, and conveys electrical signals indicative of the encoded type to a processor (not shown) employed with respiratory profile monitor 300. The processor then calibrates or otherwise adjusts the respiratory profile data according to the type of sensor attached to male attachment member 60.

Although the foregoing description contains many specificities, these should not be construed as limiting the scope of the present invention, but merely as providing illustrations of some of the presently preferred embodiments. Similarly, other embodiments of the invention may be devised which do not depart from the spirit or scope of the present invention. The scope of the invention is, therefore, indicated and limited only by the appended claims and their legal equivalents, rather than by the foregoing description. All additions, deletions and modifications to the invention as disclosed herein which fall within the meaning and scope of the claims are embraced within their scope.

What is claimed is:

1. A medical diagnostic system, comprising;
   a coupling structure including at least two interconnectable members:
   a sensor for obtaining one or more physical characteristic samples from a patient, said sensor connected to a first member of said at least two interconnectable members;
   a monitor for receiving said one or more physical characteristic samples, said monitor connected to a second member of said at least two interconnectable members; and
   an identification system for identifying a type of said sensor connected to said monitor, said identification system including an optically readable indicator element associated with said first member and an optical detector associated with said monitor for reading said optically readable indicator element.

2. The medical diagnostic system according to claim 1, and further comprising a first keying arrangement formed on a first member and a second, complementary keying arrangement formed on a second member, the first and second keying arrangements being configured with mating structural features so as to permit engagement thereof upon interconnection of said first member and said second member only if said first member and said second member are compatible for use together.

3. The medical diagnostic system according to claim 1, wherein said coupling structure includes a sealing element configured to be disposed between said first member and said second member upon interconnection thereof.

4. The medical diagnostic system according to claim 3,
   wherein said first member includes a first nipple;
   wherein said second member includes a second nipple; and
   wherein said sealing element includes a receptacle formed therethrough, said receptacle being configured to receive said first nipple and said second nipple and to create an airtight seal around both of said first nipple and said second nipple and provide a passage therebetween upon interconnection of said first member and said second member.

5. A respiratory profile evaluation system, comprising:
   a sensor for sampling at least one respiratory characteristic of a patient;
   a monitor for receiving said at least one respiratory characteristic;
   a coupling structure for operatively interconnecting said sensor and said monitor; and
   an identification structure for optically ascertaining a type of said sensor to said monitor.

6. The respiratory profile evaluation system of claim 5, further comprising calibrating data for adjusting said data representative of said at least one respiratory characteristic in accordance with said type of said sensor ascertained to said monitor.

7. The medical diagnostic system of claim 1, wherein said optical detector comprises at least one optical sensor.

8. The medical diagnostic system of claim 7, wherein said at least one optical sensor comprises a reflective optical encoder.

9. The medical diagnostic system of claim 7, wherein said at least one optical sensor generates an electrical signal based on a corresponding area of said encoding system.

10. The medical diagnostic system of claim 1, wherein said optical detector comprises a plurality of optical sensors.

11. The medical diagnostic system of claim 1, wherein said indicator element comprises a solid region or a notch through said coupling structure detectable by said optical detector.

12. The medical diagnostic system of claim 10, wherein said indicator element comprises a series of notches in said first member, a series of solid regions of said first member, or a series of a combination of notches and solid regions said first member indicative of a type of said sensor attached thereto.

13. The respiratory profile evaluation system of claim 5, wherein said identification structure comprises:
   an indicator element located on an edge of a first member of said coupling structure; and
   an identification mechanism associated with a second member of said coupling structure in a location corresponding to said edge upon interconnection of said first member and said second member.

14. The respiratory profile evaluation system of claim 13, wherein said identification mechanism comprises at least one optical sensor.

15. The respiratory profile evaluation system of claim 13, wherein said at least one optical sensor comprises a reflective optical encoder.

16. The respiratory profile evaluation system of claim 13, wherein said at least one optical sensor generates an electrical signal based on a corresponding portion of said encoding system.

17. The respiratory profile evaluation system of claim 13, wherein said identification mechanism comprises a plurality of optical sensors.

18. The respiratory profile evaluation system of claim 13, wherein said indicator element comprises a solid region or a notch through said coupling structure detectable by said identification mechanism.

19. The respiratory profile evaluation system of claim 17, wherein said indicator element comprises a series of notches in said coupling structure, a series of solid regions of said coupling structure, or a series of a combination of notches and solid regions indicative of a type of said sensor.

20. The respiratory profile evaluation system of claim 19, wherein light reflected from said solid regions differs from light reflected from a structure exposed through said notches.

* * * * *

UNITED STATES PATENT AND TRADEMARK OFFICE
CERTIFICATE OF CORRECTION

PATENT NO.       : 6,126,610
APPLICATION NO.  : 08/963336
DATED            : October 3, 2000
INVENTOR(S)      : David R. Rich and John R. Nobile It is certified that error appears in the above-identified patent and that said Letters Patent is hereby corrected as shown below:

| | | |
|---|---|---|
| COLUMN 1, | LINE 7, | change the comma after "sensors" to a period |
| COLUMN 1, | LINE 27, | change the comma after "tubes" to a period |
| COLUMN 1, | LINE 28, | before "airtight" change "a" to --an-- |
| COLUMN 2, | LINE 16, | change "sockets" to --socket.-- |
| COLUMN 2, | LINE 20, | change "ways" to --way,-- |
| COLUMN 2, | LINE 31, | at the end of the line, insert a period after "sensor" |
| COLUMN 2, | LINE 38, | insert a period after "coupling" |
| COLUMN 2, | LINE 43, | change the semicolon after "low-cost" to a comma |
| COLUMN 2, | LINE 49, | change "A" to --a-- |
| COLUMN 2, | LINE 62, | change the comma after "structure" to a period |
| COLUMN 3, | LINE 64, | change the comma after "set" to a period |
| COLUMN 4, | LINE 7, | delete the comma after "one" |
| COLUMN 4, | LINE 19, | change "relative" to --is relatively inexpensive-- |
| COLUMN 4, | LINE 37, | change "Hen" to --taken-- |
| COLUMN 5, | LINE 57, | change "a" at the end of the line to --an-- |
| COLUMN 5, | LINE 58, | change "Might" to --airtight-- |
| COLUMN 6, | LINE 1, | change the comma after "therethrough" to a period and change "Plow" to --Flow-- |
| COLUMN 6, | LINE 2, | change "we" to --are-- |
| COLUMN 6, | LINE 4, | change the comma after "respectively" to a period |
| COLUMN 6, | LINE 29, | change "1" to --7-- |
| COLUMN 6, | LINE 30, | change "a" to --an-- |
| COLUMN 6, | LINE 36, | delete the comma after "member" |
| COLUMN 6, | LINE 39, | change "sensor" to --optical detector-- |
| COLUMN 7, | LINE 10, | change "complimentary" to --complementary-- |
| COLUMN 7, | LINE 44, | insert a period after "thereof" |
| COLUMN 7, | LINE 52, | change "i" to --in-- |
| COLUMN 7, | LINE 63, | change the comma after "known" to a period |
| COLUMN 8, | LINE 10, | change "pots" to --ports-- |
| COLUMN 8, | LINE 33, | change "tube attachment" to --female-- |
| COLUMN 8, | LINE 36, | change the comma after "44" to a period |
| COLUMN 9, | LINES 15-16, | change "encoders" to --sensor-- |

UNITED STATES PATENT AND TRADEMARK OFFICE
CERTIFICATE OF CORRECTION

PATENT NO. : 6,126,610
APPLICATION NO. : 08/963336
DATED : October 3, 2000
INVENTOR(S) : David R. Rich and John R. Nobile It is certified that error appears in the above-identified patent and that said Letters Patent is hereby corrected as shown below:

| | | |
|---|---|---|
| COLUMN 9, | LINE 35, | change "12" to --72-- |
| COLUMN 9, | LINE 36, | change the comma after "63" to a period |
| COLUMN 9, | LINE 48, | change the comma after "therethrough" to a period |
| COLUMN 9, | LINE 63, | change "12," to --72,-- |
| COLUMN 10, | LINE 17, | change the comma after "notches" to a period |
| COLUMN 10, | LINE 24, | insert a period after "thereto" |
| COLUMN 10, | LINE 37, | change the comma after "10" to a period |
| COLUMN 10, | LINE 44, | change "Polarity" to --polarity-- |
| COLUMN 10, | LINE 48, | delete the comma after "ensuring" |
| COLUMN 10, | LINE 53, | change the comma after "61" to a period |
| COLUMN 10, | LINE 57, | change "member," to --number,-- |
| COLUMN 11, | LINE 21, | insert a comma after "Preferably" |
| COLUMN 11, | LINE 22, | change "sat e" to --same-- |
| COLUMN 11, | LINE 23, | change "ate" to --are-- |
| COLUMN 11, | LINE 24, | centered on its own line, after the line ending "member 10." and before the line starting "Referring" insert --Coupling and Uncoupling of the Male and Female Attachment Members"-- |
| COLUMN 11, | LINE 28, | change "Polarity" to --polarity-- |
| COLUMN 11, | LINE 30, | change "Polarity" to --polarity-- |
| COLUMN 11, | LINE 33, | delete the comma after "member" |
| COLUMN 11, | LINE 35, | change "aid" to --and-- |
| COLUMN 11, | LINE 38, | change "insesrtion" to --insertion-- |
| COLUMN 12, | LINE 5, | delete the comma after "member" |
| COLUMN 12, | LINE 18, | delete the colon after "attachment" |
| COLUMN 12, | LINE 19, | delete the colon after "The" |
| COLUMN 12, | LINE 53, | change "300" to --300, 300'-- |
| COLUMN 12, | LINE 56, | change "Female" to --female- |

UNITED STATES PATENT AND TRADEMARK OFFICE
CERTIFICATE OF CORRECTION

PATENT NO. : 6,126,610
APPLICATION NO. : 08/963336
DATED : October 3, 2000
INVENTOR(S) : David R. Rich and John R. Nobile It is certified that error appears in the above-identified patent and that said Letters Patent is hereby corrected as shown below:

CLAIM 1, COLUMN 13, LINE 16, change the colon after "members" to a semicolon
CLAIM 2, COLUMN 13, LINE 31, at the beginning of the line, before "further" delete "and"
CLAIM 12, COLUMN 14, LINE 24, after "regions" and before "said" insert --in--

Signed and Sealed this

Seventeenth Day of October, 2006

JON W. DUDAS
*Director of the United States Patent and Trademark Office*